US008792618B2

(12) United States Patent
Mruthyunjaya et al.

(10) Patent No.: US 8,792,618 B2
(45) Date of Patent: Jul. 29, 2014

(54) RADIOGRAPHIC DETECTOR INCLUDING BLOCK ADDRESS PIXEL ARCHITECTURE, IMAGING APPARATUS AND METHODS USING THE SAME

(75) Inventors: Ravi K. Mruthyunjaya, Penfield, NY (US); Timothy J. Tredwell, Fairport, NY (US); Jeff Hsin Chang, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 445 days.

(21) Appl. No.: 13/341,967

(22) Filed: Dec. 31, 2011

(65) Prior Publication Data
US 2013/0170616 A1    Jul. 4, 2013

(51) Int. Cl.
*H01L 27/146* (2006.01)
*H01L 27/10* (2006.01)
*G01T 1/24* (2006.01)

(52) U.S. Cl.
USPC ............... 378/98.8; 250/370.09; 250/370.14

(58) Field of Classification Search
USPC ................ 378/19, 91, 98.8, 189, 204, 210; 250/370.01, 370.08, 370.09, 370.11, 250/370.12, 370.13, 370.14, 371, 526
See application file for complete search history.

(56) References Cited

U.S. PATENT DOCUMENTS

| 5,148,268 | A | 9/1992 | Tandon et al. |
|---|---|---|---|
| 5,970,115 | A | 10/1999 | Colbeth et al. |
| 6,235,576 | B1 | 5/2001 | Hong et al. |
| 6,646,249 | B2 | 11/2003 | Bird |
| 7,601,961 | B2 | 10/2009 | Franklin et al. |
| 2005/0285043 | A1 | 12/2005 | Nascetti et al. |
| 2007/0013798 | A1 | 1/2007 | Ahn et al. |
| 2009/0095914 | A1 | 4/2009 | Goo et al. |
| 2009/0173974 | A1 | 7/2009 | Shah et al. |
| 2010/0141820 | A1 | 6/2010 | Chenebaux et al. |

FOREIGN PATENT DOCUMENTS

EP    0 707 417    4/1996

OTHER PUBLICATIONS

International Search Report mailed Mar. 29, 2013 for International Application No. PCT/US2012/068118, 3 pages.

*Primary Examiner* — Anastasia Midkiff

(57) ABSTRACT

Embodiments of radiographic imaging systems; digital radiography detectors and methods for using the same can include radiographic imaging pixel unit cells that can include a plurality of N pixel elements that each include a photoelectric thin-film conversion element connected in-series to a conversion thin-film switching element, a conductor connected to the plurality of N pixel elements and an output switching element connected between the conductor and an imaging array output. Scan lines or row lines can extend in a first direction coupled to more than one pixel unit cell and data lines or column lines can extend in a second direction coupled to more than one pixel unit cell.

20 Claims, 15 Drawing Sheets

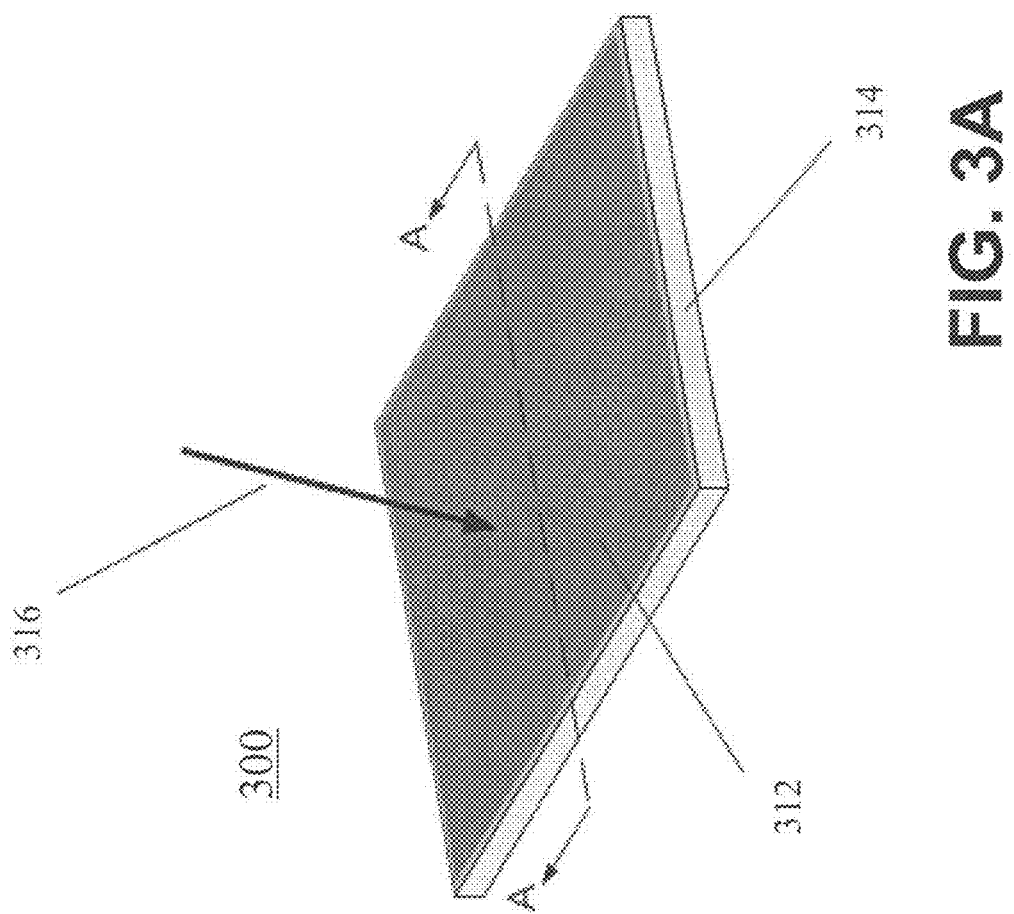

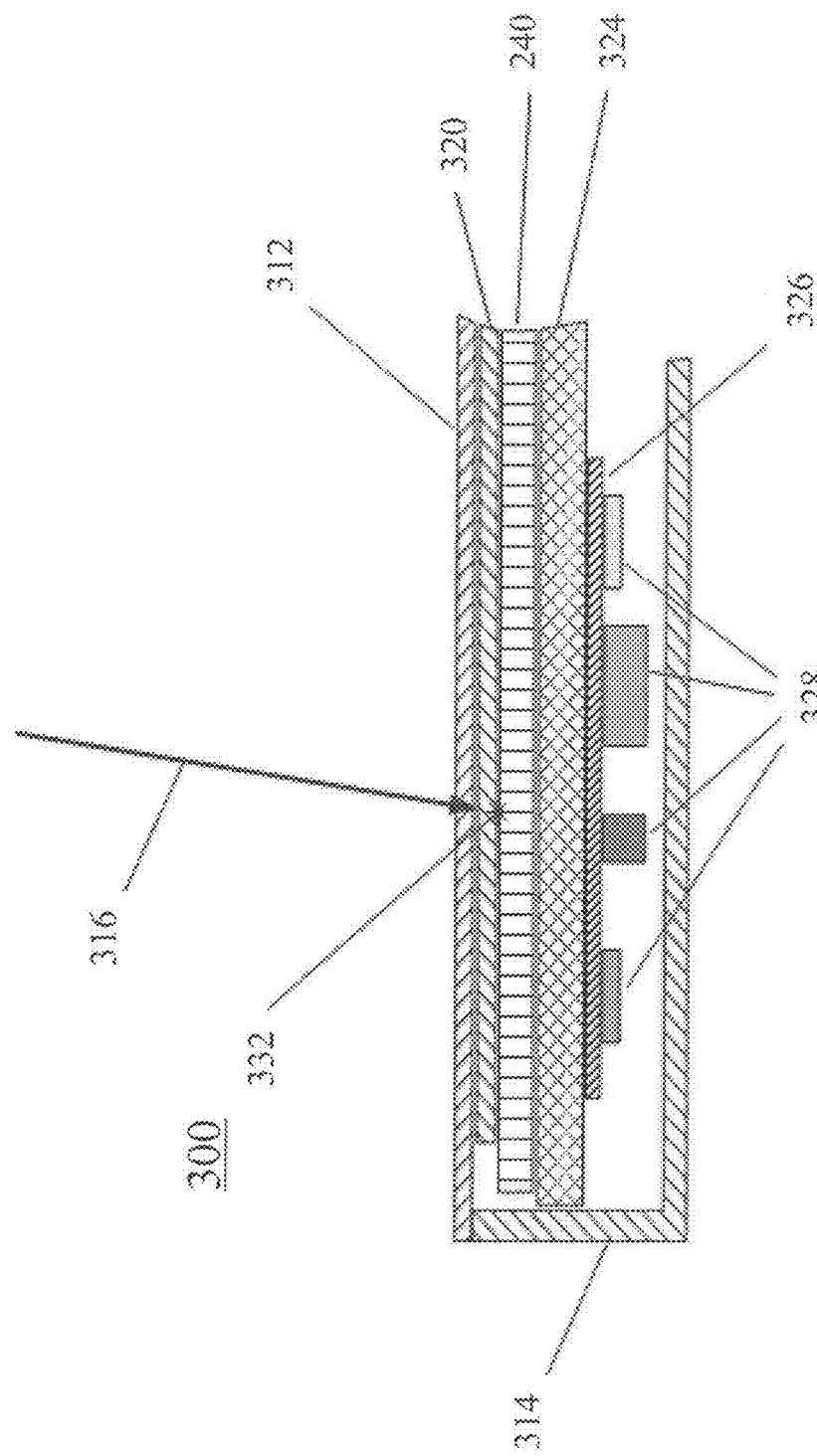

RADIOGRAPHIC DETECTOR INCLUDING BLOCK ADDRESS PIXEL ARCHITECTURE, IMAGING APPARATUS AND METHODS USING THE SAME

FIELD OF THE INVENTION

The invention relates generally to the field of medical imaging, and in particular to radiographic imaging and digital radiographic (DR) detectors and more particularly to pixel structure or pixel layout related to the use of non-single crystalline materials in sensors.

BACKGROUND

Stationary radiographic imaging equipment are employed in medical facilities (e.g., in a radiological department) to capture medical x-ray images on x-ray detector. Mobile radiographic carts can include an x-ray source used to capture (e.g., digital) x-ray images on x-ray detector. Such medical x-ray images can be captured using various techniques such as computed radiography (CR) and digital radiography (DR) in radiographic detectors.

A related art digital radiography (DR) imaging panel (e.g., flat panel detector) acquires image data from a scintillating medium using an array of individual sensors, arranged in a row-by-column matrix, in which each sensor provides a single pixel of image data. Each pixel generally includes a photosensor and a switching element that can be arranged in a planar or a vertical manner, as is generally known in the art. In these imaging devices, hydrogenated amorphous silicon (a-Si:H) is commonly used to form the photodiode and the thin-film transistor switch needed for each pixel. DR detectors can include several thousands of picture elements, or pixels. In one known imaging arrangement, a frontplane has an array of photosensitive elements, and a backplane has an array of thin-film transistor (TFT) switches.

A traditional unit cell pixel architecture design used in digital radiographic applications would contain 1 transistor element and 1 photodiode element. A row of transistor elements would be controlled by a common row select control signal that can connect photodiode elements to their respective output column (e.g., data line).

However, there is a need for improvements in the consistency and/or quality of medical x-ray images, particularly when obtained by an x-ray apparatus designed to operate with a-Si DR x-ray detectors.

SUMMARY OF THE INVENTION

An aspect of this application is to advance the art of medical digital radiography.

Another aspect of this application to address in whole or in part, at least the foregoing and other deficiencies in the related art.

It is another aspect of this application to provide in whole or in part, at least the advantages described herein.

An aspect of this application to is to provide methods and/or apparatus to address and/or reduce disadvantages caused by the use of portable (e.g., wireless) digital radiography (DR) detectors and/or radiography imaging apparatus using the same.

An aspect of this application to is to provide radiographic imaging methods and/or apparatus that can reduce a number of datalines for a radiographic imaging array.

An aspect of this application to is to provide radiographic imaging methods and/or apparatus that can provide pixel unit cells that each can include N pixel output control units and N photosensor elements across N pixel columns to selectively connect to a single output dataline. In one embodiment, the N pixel output control units across N pixel columns in the pixel unit cell can be controlled by N additional, separate and independent control signals.

An aspect of this application to is to provide radiographic imaging methods and/or apparatus that can provide nit pixel architecture embodiments that can add one additional switching element across N columns or rows. In one embodiment, the one additional switching element can selectively couple each of N photosensor elements in a pixel unit cell to a common dataline output, where N is a positive integer greater than 2.

An aspect of this application to is to provide radiographic imaging methods and/or apparatus that reduce noise generated in a radiographic imaging array.

In accordance with one embodiment, the present invention can provide a radiographic imaging array, can include an insulating substrate; a scan line to extend in a first direction over the insulating substrate; a data line to extend in a second direction over the insulating substrate; and a thin film pixel unit cell including a first thin film switching element including a first terminal; a second terminal electrically coupled to the data line; and a control terminal electrically coupled to the scan line, wherein the first terminal and the second terminal are electrically coupled based on a scan signal from the scan line; a plurality of N pixel elements each comprising a photoelectric thin film conversion element and a second thin film switching element, where the photoelectric thin film conversion element and the second thin film switching element are connected in-series between a first reference voltage and a first terminal of the first switching element.

In accordance with one embodiment, the present invention can provide a method of forming a digital radiographic detector including an indirect imaging pixel array, the method can include providing a scintillator for an indirect imaging pixel array; providing an insulating substrate for the indirect imaging pixel array; providing scan lines extending in a first direction; providing data lines extending in a second direction; and providing pixel unit cells, each pixel unit cell including a first thin-film transistor element; a plurality of N pixel elements each comprising pairs of photoelectric thin film conversion element and a second thin-film transistor where each pair of the photoelectric thin film conversion element and the second thin-film transistor are connected in series between a first reference voltage and the first switching element, wherein the first thin-film transistor selectively connects said each pair of the photoelectric conversion element and the second thin-film transistor to a single dataline within the pixel unit cell.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 3A shows a perspective view of a portable wireless DR detector that can have utility in radiography imaging apparatus applications.

FIG. 3B is a diagram that shows a portion of a cross-sectional view along section line A-A of the portable wireless DR detector of FIG. 3A.

DESCRIPTION OF EXEMPLARY EMBODIMENTS

Figure 1:
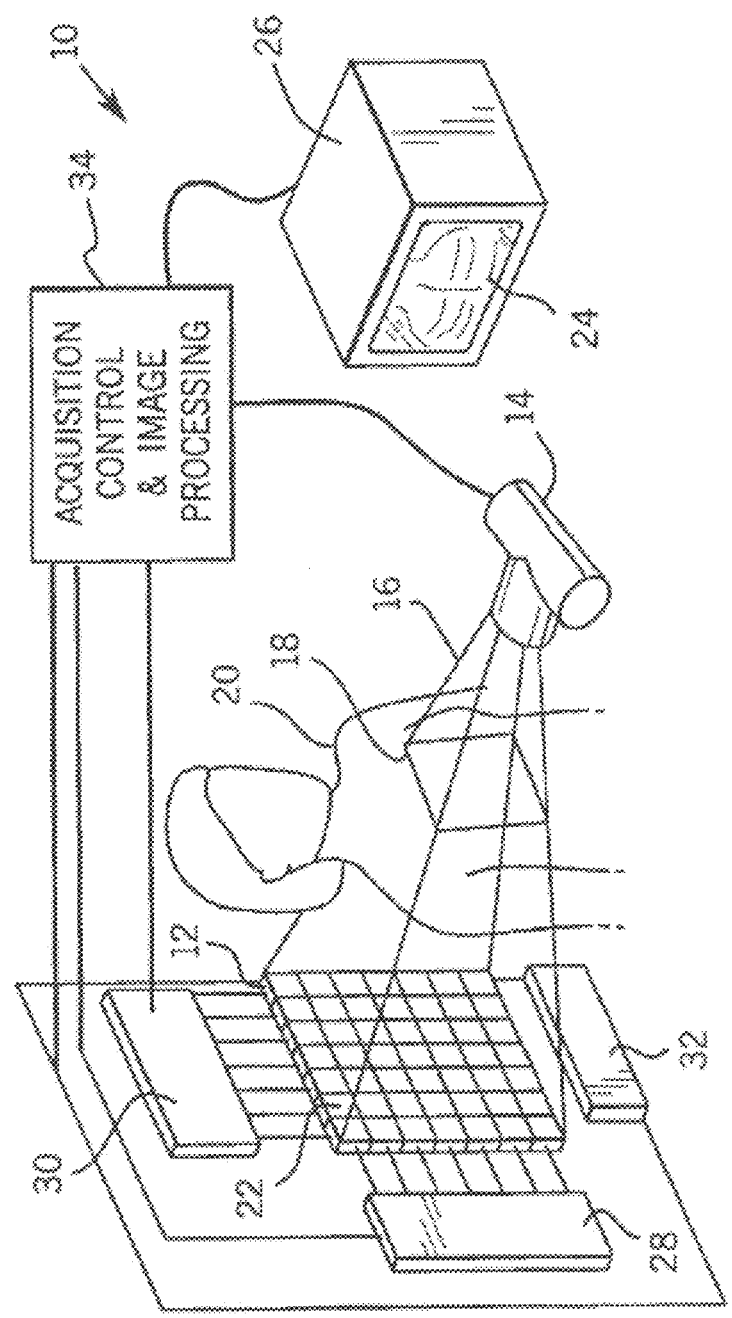
FIG. 1 is a diagram that shows a perspective view of a radiographic imaging apparatus including an area detector according to the present application used for a radiographic procedure.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a diagram that shows a perspective view of an exemplary area detector configured to include rows and columns of detector cells in position to receive x-rays passing through a patient during a radiographic procedure. As shown in FIG. 1, an x-ray system 10 that can use an area array 12 can include an x-ray tube 14 collimated to provide an area x-ray beam 16 passing through an area 18 of a patient 20. The beam 16 can be attenuated along its many rays by the internal structure of the patient 20 to then be received by the detector array 12 that can extend generally over a prescribed area (e.g., a plane) perpendicular to the central ray of the x-ray beam 16.

The array 12 can be divided into a plurality of individual cells 22 that can be arranged rectilinearly in columns and rows. As will be understood to those of ordinary skill in the art, the orientation of the columns and rows is arbitrary, however, for clarity of description it will be assumed that the rows extend horizontally and the columns extend vertically.

In exemplary operations, the rows of cells 22 can be scanned one (or more) at a time by scanning circuit 28 so that exposure data from each cell 22 can be read by read-out circuit 30. Each cell 22 can independently measure an intensity of radiation received at its surface and thus the exposure data read-out can provide one pixel of information in an image 24 to be displayed on a display 26 normally viewed by the user. A bias circuit 32 can control a bias voltage to the cells 22.

Each of the bias circuit 32, the scanning circuit 28, and the read-out circuit 30, can communicate with an acquisition control and image processing circuit 34 that can coordinate operations of the circuits 30, 28 and 32, for example, by use of an electronic processor (not shown). The acquisition control and image processing circuit 34, can also control the examination procedure, and the x-ray tube 14, turning it on and off and controlling the tube current and thus the fluence of x-rays in beam 16 and/or the tube voltage and hence the energy of the x-rays in beam 16.

The acquisition control and image processing circuit 34 can provide image data to the display 26, based on the exposure data provided by each cell 22. Alternatively, acquisition control and image processing circuit 34 can manipulate the image data, store raw or processed image data (e.g., at a local or remotely located memory) or export the image data.

Exemplary pixels 22 can include a photo-activated image sensing element and a switching element for reading a signal from the image-sensing element. Image sensing can be performed by direct detection, in which case the image-sensing element directly absorbs the X-rays and converts them into charge carriers. However, in most commercial digital radiography systems, indirect detection are used, in which an intermediate scintillator element converts the X-rays to visible-light photons that can then be sensed by a light-sensitive image-sensing element.

Examples of image sensing elements used in image sensing arrays 12 include various types of photoelectric conversion devices (e.g., photosensors) such as photodiodes (P-N or PIN diodes), photo-capacitors (MIS), or photoconductors. Examples of switching elements used for signal read-out include MOS transistors, bipolar transistors, FETs, TFTs or switch components.

Figure 2:
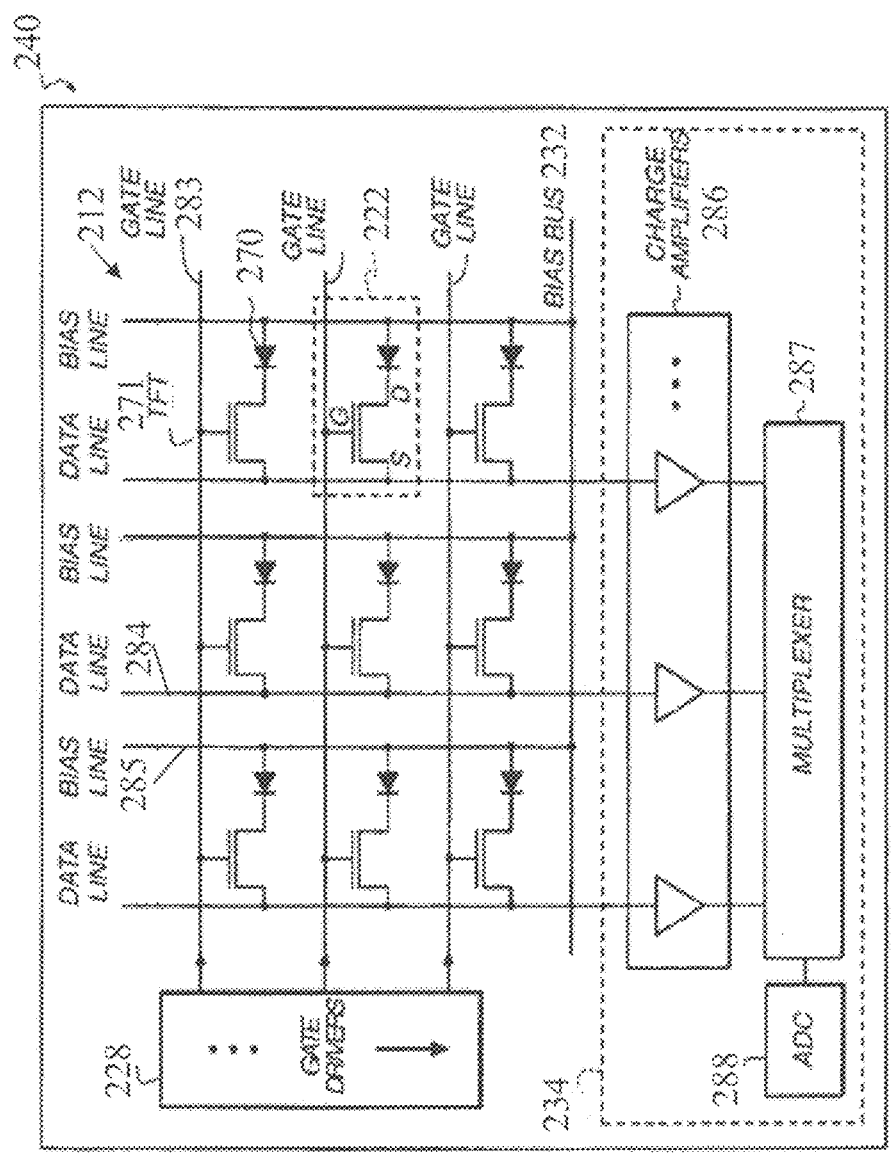
FIG. 2 is a diagram that shows schematic of a portion of an exemplary imaging array for a radiographic detector according to the application.

FIG. 2 is a diagram that shows a schematic of a portion of an exemplary related art imaging array for a radiographic detector according to the application. As shown in FIG. 2, a schematic of a portion of an exemplary flat panel imager 240 can include an imaging array 212 having a number of a-Si:H n-i-p photodiodes 270 and TFTs 271. An exemplary cell 222 can include a photodiode 270 having its cathode connected to the source (e.g., drain) of an FET 271. A bias circuit 232 can control a bias voltage to the cells 222. Gate driver chips 228 can connect to the blocks of gate lines 283 and readout chips 234 (e.g., Read Out Integrated Circuits (ROICs)) connect to blocks of data lines 284. Charge amplifiers 286 can be provided that receive signals from the data lines 284. An output from the charge amplifiers 286 can go to an analog multiplexer 287 or directly to an analog-to-digital converter (ADC) 288 to stream out the digital image data at desired rates.

In an exemplary hydrogenated amorphous silicon (a-Si:H) based indirect flat panel imager, incident X-ray photons are converted to optical photons, which are subsequently converted to electron-hole pairs within the a-Si:H n-i-p photodiodes 270. The pixel charge capacity of the photodiodes is a product of the bias voltage and the photodiode capacitance. In general, a reverse bias voltage is applied to the bias lines 285 to create an electric field (e.g., and hence a depletion region) across the photodiodes and enhance charge collection efficiency. The image signal can be integrated by the photodiodes while the associated TFTs 271 are held in a non-conducting ("off") state, for example, by maintaining the gate lines 283 at a negative voltage. The array 212 can be read out by sequentially switching rows of the TFTs 271 to a conducting state using TFT gate control circuitry. When a row of pixels is switched to a conducting ("on") state, for example by applying a positive voltage to the corresponding gate line 283, charge from those pixels can be transferred along data lines 284 and integrated by external charge-sensitive amplifiers 286. After data is read out, the row can then be switched back to a non-conducting state, and the process is repeated for each row until the entire array has been read out. The signal outputs from the external charge-sensitive amplifiers 286 are transferred to an analog-to-digital converter (ADC) 288 by a parallel-to-serial multiplexer 287, subsequently yielding a digital image. The flat panel imager having an imaging array 212 as described with reference to FIG. 2 is capable of both single-shot (e.g., static, radiographic) and continuous (e.g., fluoroscopic) image acquisition.

FIG. 3A shows a perspective view of a portable wireless DR detector 300 according to embodiments of the application that can have utility in radiography imaging apparatus applications. FIG. 3B shows a portion of a cross-section view along line A-A of the DR detector 300. As shown in FIGS. 3A-3B, the portable DR detector 300 can enclose the imager 240 including the imaging array 212.

In one embodiment, the DR detector 300 can include an enclosure 314 including top panel cover 312 made of material that passes x-ray flux 316 without significant attenuation. Scintillator 320 can be under (e.g., directly connected) the cover 312, the imaging array 212 can be under the scintillator 320, and readout electronics can be co-planar with the imaging array 212, partially below support member 324 or on a flexible connecter therebetween. The support member 324 can be included to securely and/robustly mount the imager 240 and can further operate as a shock absorber between components therein and the enclosure 314. The x-ray flux 316 can pass through the top panel cover 312, impinge upon scintillator 320 where stimulation by high-energy photons in the x-ray flux 316 can cause the scintillator 320 to emit low energy photons 332 for detection by the imaging array 212. Device electronics required for proper operation of the detector 300 can be mounted within the enclosure 314 and can include electronic components 328 (e.g., processors, FPGAs, ASICs, chips, etc.) that can be mounted on one or more separate and/or interconnected circuit boards 326.

In the pixel architecture shown in FIG. 2, the number of datalines 284 or column outputs is equal to the number of photodiodes 270 or pixel columns Therefore, the numbers of external ROIC input connections are equal to the number of pixel unit cell columns For example, in the case of 1024 pixel columns, there are 1024 dataline external connections required. Exemplary commercially available external ROIC IC solutions can handle 64 or 256 dataline inputs and therefore multiple ROIC assemblies are used to satisfy a total of 1024 dataline output columns. For the above example, 16 64 ROIC IC assemblies or 4 256 ROIC IC assemblies can be used. Numerous ROIC IC assemblies can become a significant portion of the overall radiographic detector cost and may not be a feasible approach for lower cost radiographic applications.

Embodiments of a novel pixel architecture can include pixel unit cells, where each pixel unit cell can include N pixel output control units (e.g., N TFT elements or switches) and N photosensor elements across N pixel columns and 1 additional TFT that can then selectively connect a single output dataline (e.g., shared) to the N TFT elements across N pixel columns Embodiments of a pixel unit cell can include N unit pixels (e.g., each unit pixel with a TFT element and a thin-film photosensor element) and one additional pixel output control unit to selectively couple the N unit pixels of a pixel unit cell to a shared dataline.

Embodiments of novel pixel architectures and methods or apparatus for using the same for digital radiographic applications are described herein. Unit pixel architecture embodiments can add one additional thin-film element (e.g., transistor) across N columns. According to certain exemplary embodiments, the one additional thin-film transistor (TFT) can connect each of the N TFT elements associated with N thin-film photosensor elements to a common dataline column output where N is a positive integer greater than 2. The one additional TFT can be controlled by a single common row select control signal. The N TFT elements across N pixel columns in the unit pixel architecture embodiments can be controlled by N additional, separate and independent control signals (e.g., block address TFT elements). In exemplary embodiments, to connect a photosensor to a dataline, a specific photosensor (e.g., in N block address TFTs) and a specific row (e.g., row select TFT) can be enabled together or concurrently. In certain exemplary embodiments, digital radiographic imaging detectors can include thin-film elements such as but not limited to thin-film photosensors and thin-film transistors. Thin film circuits can be fabricated from deposited thin films on insulating substrates as known to one skilled in the art of radiographic imaging. Exemplary thin film circuits can include amorphous-silicon devices such as a-Si PIN diodes, schottky diodes, MIS photocapacitors, and be implemented using amorphous semiconductor materials, polycrystalline semiconductor materials such as silicon, or single-crystal silicon-on-glass (SiOG).

Figure 4:
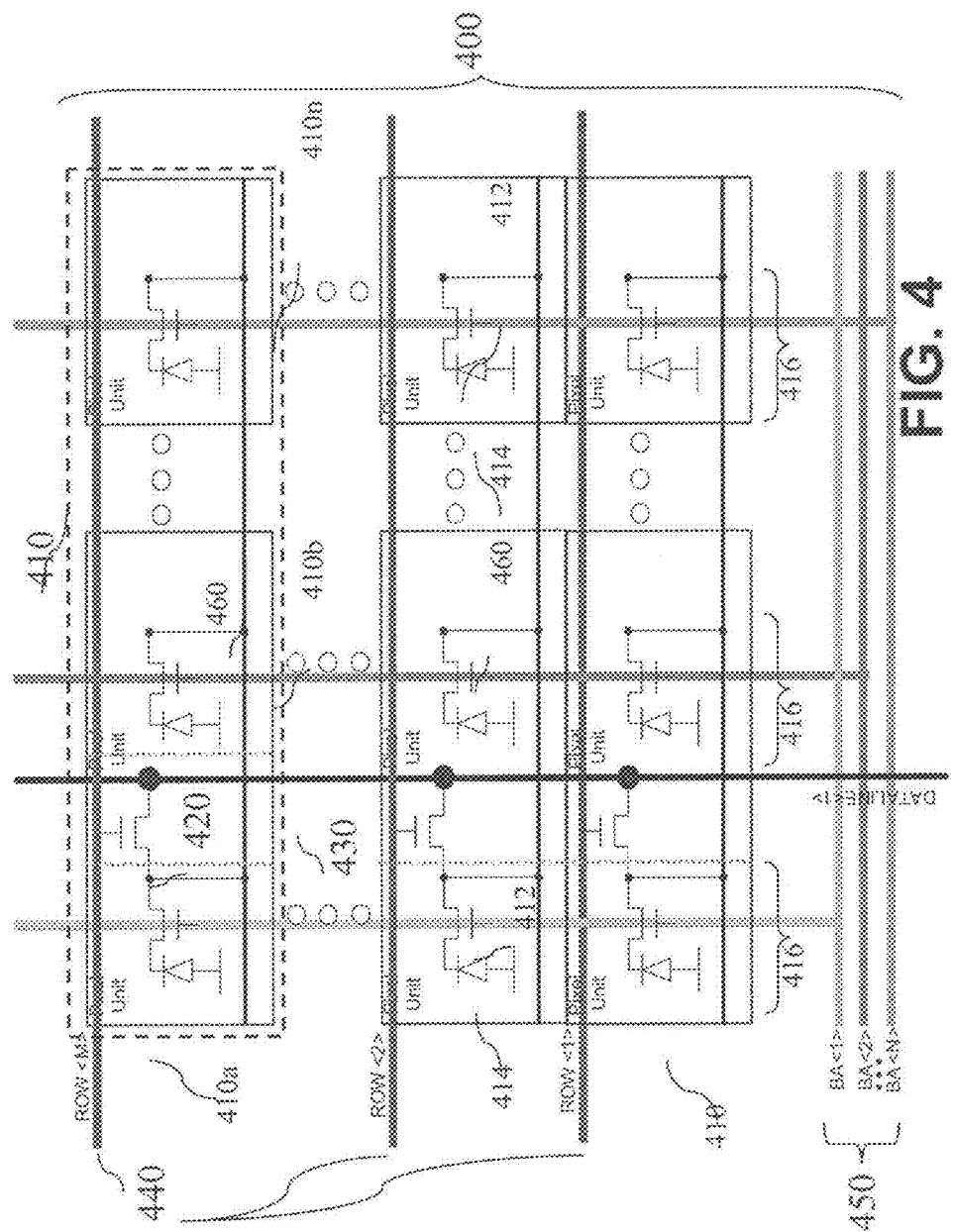
FIG. 4 is a diagram that shows an exemplary DR imaging array including an embodiment of a unit pixel architecture for a DR detector according to the application.

FIG. 4 is a diagram that shows an embodiment of a pixel unit cell for a DR detector according to the application. As shown in FIG. 4, pixel unit cell 410 can use one additional selector 420 across N photosensors 414 respectively in N pixel elements 410a, 410b, . . . , 410n in columns 416. The selector 420 can electrically couple each of N TFT elements 412 with a common dataline 430 output or column output. The selector 420 can be controlled by a row select control signal 440 (ROW<1>, ROW<2>, . . . , ROW<m>). The N TFT 412 elements for N pixels 410a, 410b, . . . , 410n across N pixel columns 416 can be controlled by N separate and independent control signals 450 (BA<1>, BA<2>, . . . , BA<N>) (e.g., block address TFTs). The N TFT elements 412 selectively couple the photosensors 414 to the selector 420 using a intra-pixel unit cell connector 460. To connect a photodiode 414 in the pixel unit cell 410 to a dataline 430, a specific one of the TFTs 412 and selector 420 (e.g., row select) can both be enabled together.

Embodiments according to the applications can provide various advantages. For example, the N TFT elements 412 in the pixel unit cell 410 can reduce the number of datalines 430 in a DR imaging array 400 by the number of independent control signals (e.g., a ratio of N). For example, in the case of 1024 pixel columns and N=8 separate unit pixel control signals there can be 128 dataline external connections required compared to 1024 for a related art pixel architecture. Reducing a number of external dataline connections means that fewer ROIC IC assemblies can be used. In the above example, 2 64 ROIC IC assemblies can be used in contrast to 16 64 ROIC IC assemblies or 4 256 ROIC IC assemblies used for 1024 pixel columns or datalines as shown in FIG. 2.

Another advantage to TFT elements 412 is that multiple unit pixel control signals 450 can be enabled simultaneously to allow the charge of multiple photosensors or photodiode elements (e.g., horizontally) to be transferred to one dataline 430 output at one time (e.g., charge binning). Concurrently reading multiple photosensor elements can increase a signal to noise (SNR) ratio.

Further advantages to TFT elements 412 with independent control (e.g., signals 450) is that subsampling of a pixel unit cell 410 for DR imaging array 400 can be performed. Individual TFTs 412 may or may not be selected to allow for photodiode element charge subsampling within the pixel unit cell 410. For example, not addressing or skipping block address TFTs can represent horizontal sub-sampling of the pixel unit cell 410 or the DR imaging array 400.

An additional advantage is that charge binning and/or subsampling can be done vertically in pixel unit cell 410 for the DR imaging array 400 by accessing multiple rows 440. Given M rows 440, multiple row select signals can be accessed simultaneously for charge binning (e.g., adding together charge for photosensors in up to M rows), which can represent vertical charge binning. Further, for M rows 440, specific rows within M rows can be skipped or not accessed, which can represent vertical subsampling. Further, horizontal charge binning and/or subsampling and vertical charge binning and/or subsampling can be performed concurrently using the pixel unit cell 410.

Figure 5:
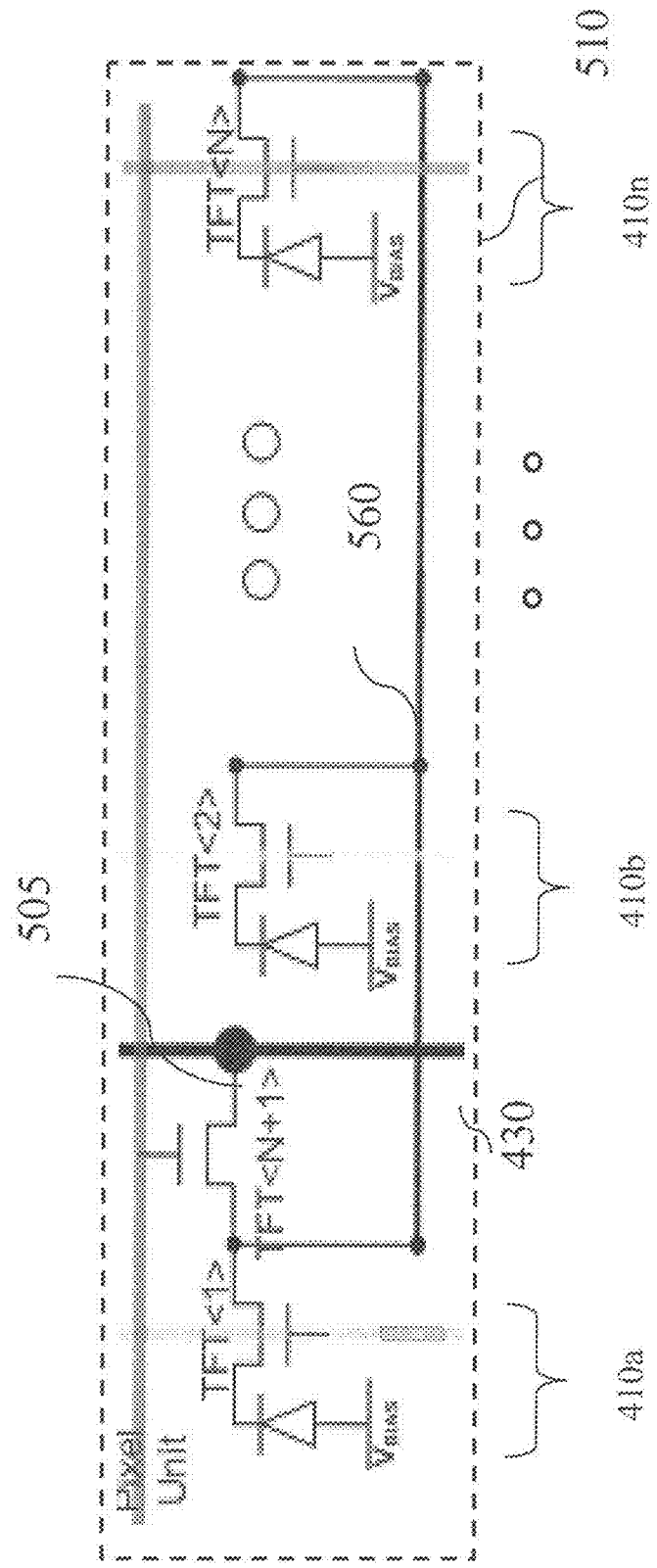
FIG. 5 is a diagram that shows a pixel unit cell embodiment using N pixels and N+1 TFT elements according to the application.

FIG. 5 is a diagram that shows an embodiment of a pixel unit cell for a DR detector according to the application. As shown in FIG. 5, N pixel unit cells 410 can be repeatedly formed or laid out in pixel unit cell 510 where N is the number of pixel block addresses contiguous or extending in one direction that can share a common output 505 for improved fill factor. In one embodiment, the pixel unit cell 510 can contain N+1 TFTs for selectable pixels. The common output 505 between the TFTs can allow for a one output (e.g., dataline 430). As shown in FIG. 5, the pixel unit cell can connect unit pixels 410a, 410b, . . . , 410n to node 505 using unit pixel connector 560.

For example, intra-pixel block sharing can reduce the overall dataline capacitance compared to combining multiple vertical datalines together outside the imaging data array. Further, reduced dataline capacitance can reduce noise (e.g., thermal noise in the imaging array).

Embodiments of DR detector imaging arrays including independent pixel addressing and methods for using the same can allow for combining and/or skipping photosensor elements in the horizontal direction within a pixel unit cell. Embodiments of a pixel unit cell (e.g., using an additional TFT inside the pixel unit cell) can reduce or minimize an amount of column charge injection, which can be caused by multiplexing control signals. In an exemplary DR detector application, the dataline can be connected to a ROIC that can put the dataline into at least two states, which can include a reset state and an integration state. In a first state or the reset state, any charge collected or injected to the dataline that is connected to the ROIC can be removed. Thus, as a multiplexing switch can be located farther from the ROIC and closer to (e.g., within) the pixel unit cell, more dataline routing exists that can be reset by the ROIC. In the case of an end of column multiplexing architecture, a pixel array dataline side can be as long as the pixel array and susceptible to any and/or all horizontal (e.g., row-based) and/or vertical (e.g., column based) control signals. In one embodiment according to the application, a pixel array dataline side can be small or right at the pixel unit cell and can be only dependent on its' single horizontal (e.g., row-based) and/or vertical (e.g., column based) control signals. For example, increasing or maximizing the ROIC dataline side that can be placed in a reset state can reduce opportunities for noise or injection charge.

Further, when a different number of switching events occurs because of readout configuration (e.g., subsampling or binning), differences in the number of feedthrough events can create readout specific configuration artifacts. Embodiments of a pixel architecture less susceptible to injection charge outside of a pixel unit cell can reduce or avoid readout configuration artifacts based on running different subsampling and binning modes where pixels can be skipped or combined (e.g., vice full readout modes).

Figure 6:
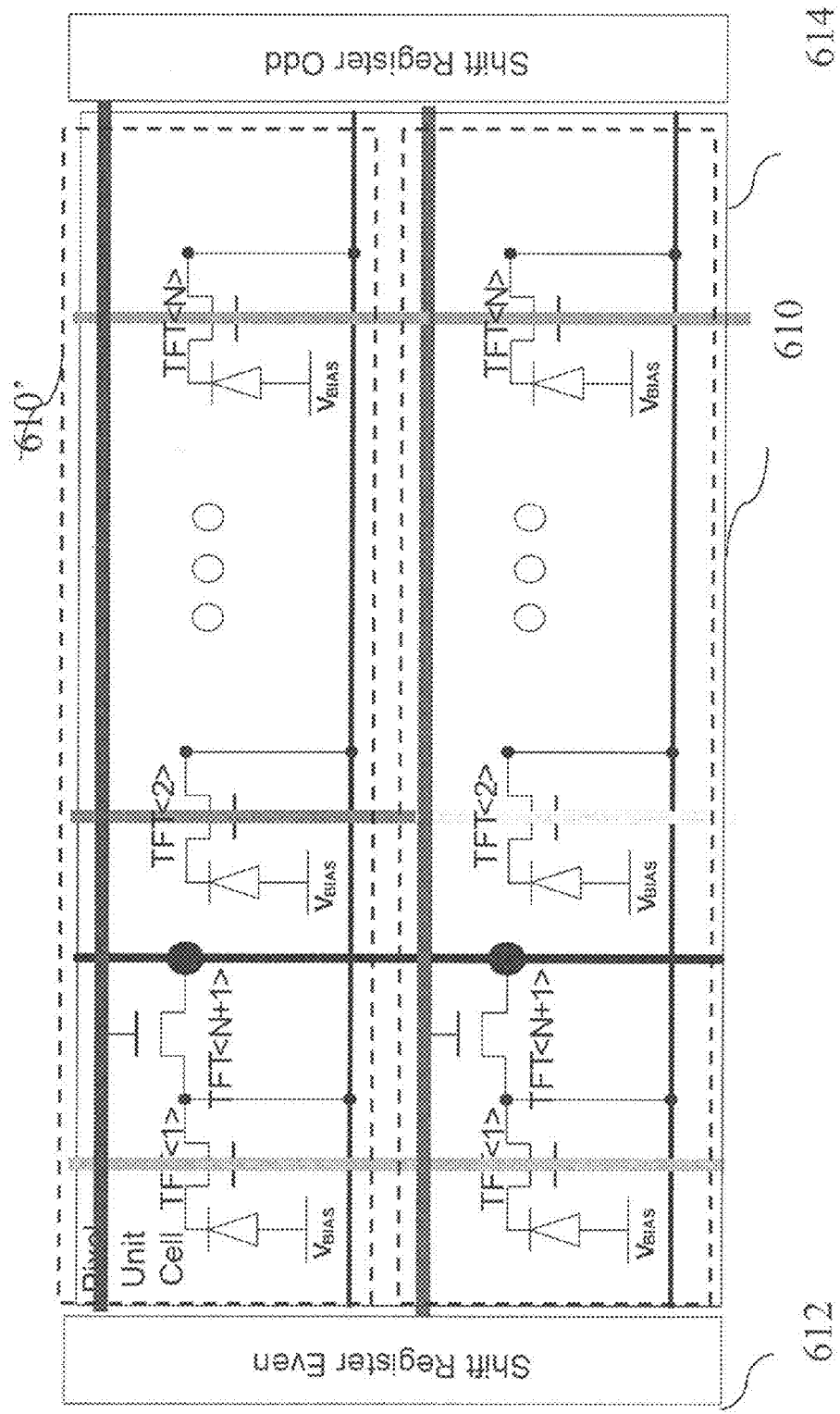
FIG. 6 is a diagram that shows a portion of an exemplary DR imaging array including an embodiment of pixel unit cells according to the application.

From a radiographic imaging system or DR detector perspective, a readout scheme can use, but is not limited to, an equal spatial subsampling frequency in the vertical direction just as in the horizontal direction. Embodiments according to the application can implement an imaging array architecture with equal (e.g., two) independently controlled row shift registers, for example, where one can control even rows and another can control odd rows. FIG. 6 is a diagram that shows a portion of an exemplary DR imaging array including pixel unit cell embodiment 16 pixels wide, which can use 17 TFT elements. As shown in FIG. 6, even rows can contain pixel unit cells 610 in a given row that can be controlled by a shift register 612 physically located on the left side (e.g., a first side) and odd rows can contains pixel unit cells 610' in a given row that can be controlled by a shift register 614 physically located on the right (e.g., a second side).

To readout all photosensors (e.g., photodiodes 414) in the array can require using the left shift 612 register row driver N times for all pixels in the even rows to readout N independently controlled block address pixel elements in the even rows and then can require using the right shift register 614 row driver an additional N times for all pixels in the odd rows to readout N independently controlled block address pixel elements in the odd rows. Thus, up to a total of 2N sub-frames can be used to readout all pixel elements as shown in FIG. 6.

Figure 7:
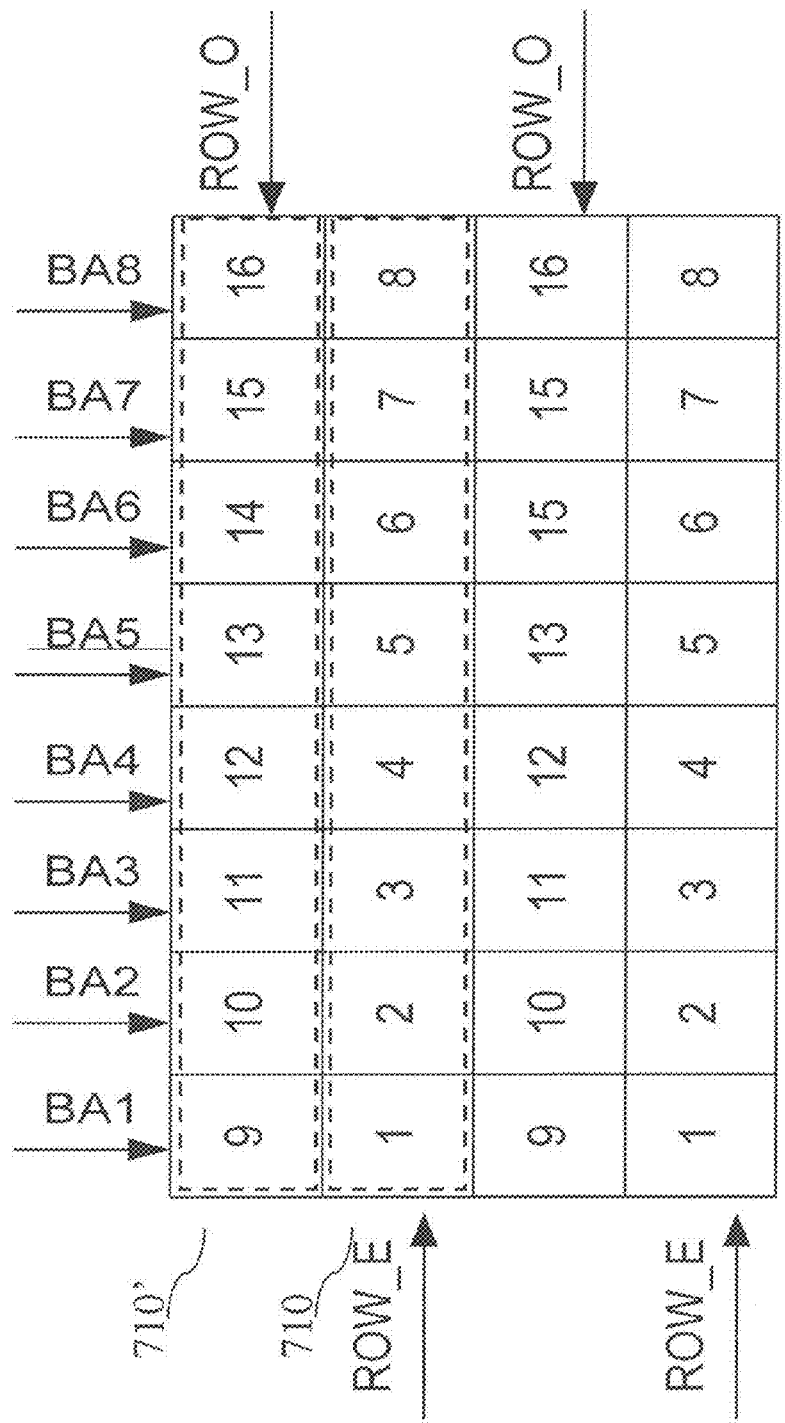
FIG. 7 is a diagram that shows a portion of an exemplary DR imaging array including an embodiment of pixel unit cells according to the application.

FIG. 7 is a diagram that shows a portion of another exemplary DR imaging array including an embodiment of pixel unit cells according to the application. Pixel unit cells 710 can be 8 pixels elements wide and can use 9 switching elements. As shown in FIG. 7, a portion of an exemplary DR imaging array can represent 4 rows and 8 columns and illustrate a sub-frame readout sequence. As shown in FIG. 7, a left side register can read pixel unit cell 710 and a right side register can read pixel unit cell 710' and 16 sub-frame readouts can be used to readout all pixel elements for an 8 wide pixel unit cell architecture.

Figure 8:
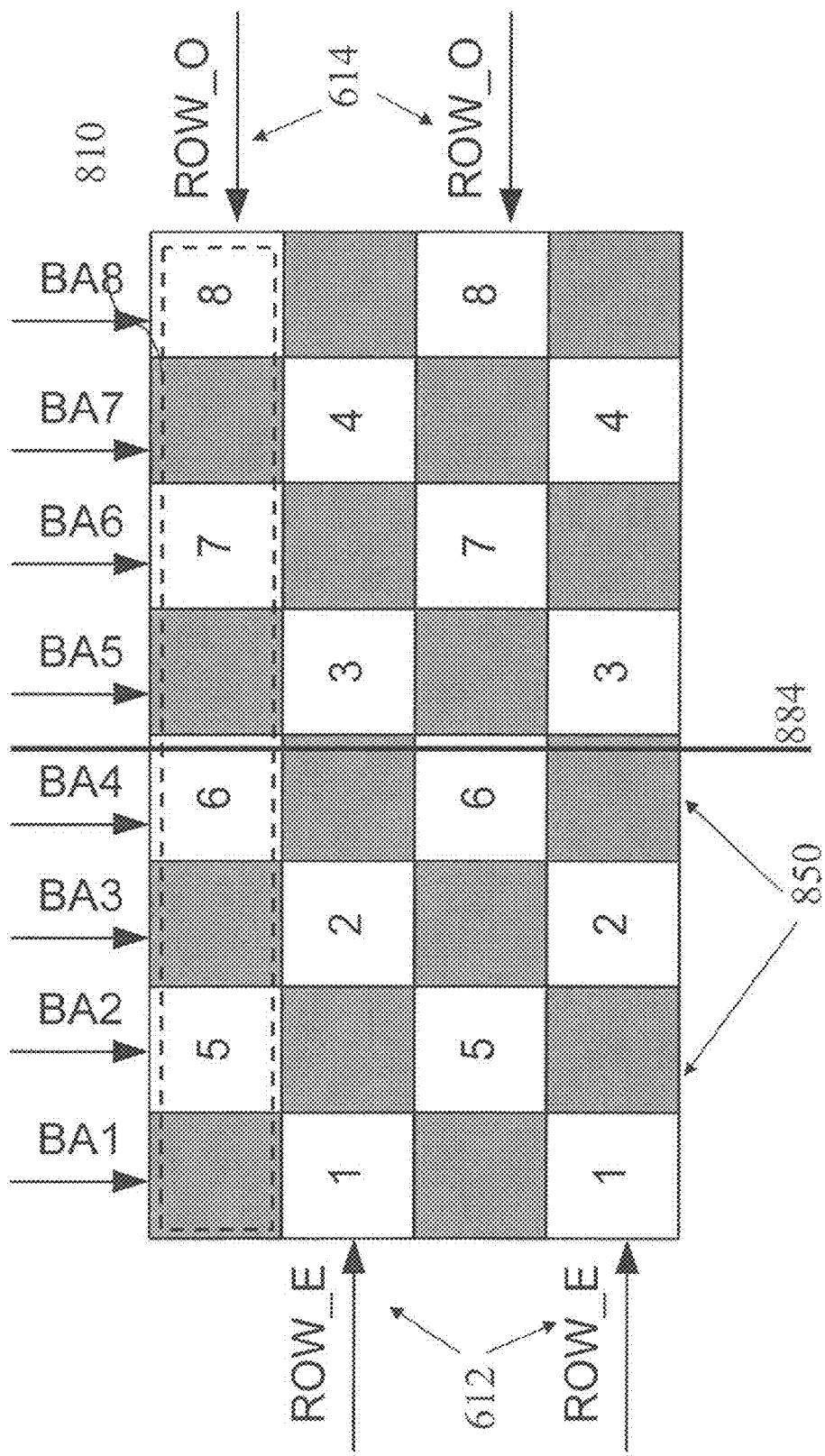
FIG. 8 is a diagram that shows a portion of an exemplary DR imaging array including an embodiment of pixel unit cells according to the application.

FIG. 8 is a diagram that shows a portion of an exemplary DR imaging array including an embodiment of pixel unit cells according to the application. Pixel unit cells 810 can be 8 pixels elements wide and can use 9 switching elements. As shown in FIG. 8, a sub-sampling architecture (e.g., sub-sampling by 2) can reduce the number of sub-frame readouts. As shown in FIG. 8, a lower resolution image would result. In one example, the first 4 sub-frames 1, 2, 3, and 4 using block address control signals BA1, BA3, BA5, and BA7 are read using the left shift register 612. Then, the second 4 sub-frames 5, 6, 7, and 8 using block address control signals BA2, BA4, BA6, and BA8 can be read using the right shift register 614. A total of N sub-frames can be required for the sub-sample-by-2 implementation as shown in FIG. 8, where N is equal to 8. Exemplary grey regions 850 can represent unused or not-required pixel elements. To achieve this particular horizontal pattern, N must be equal to or greater than 4 in a pixel unit cell. As shown in FIG. 8, the imaging array architecture can allow for only one dataline 884 (e.g., vertical) to be present within the imaging array for any pixel unit cell horizontal pattern up to a pattern of N photosensors.

Figure 9A:
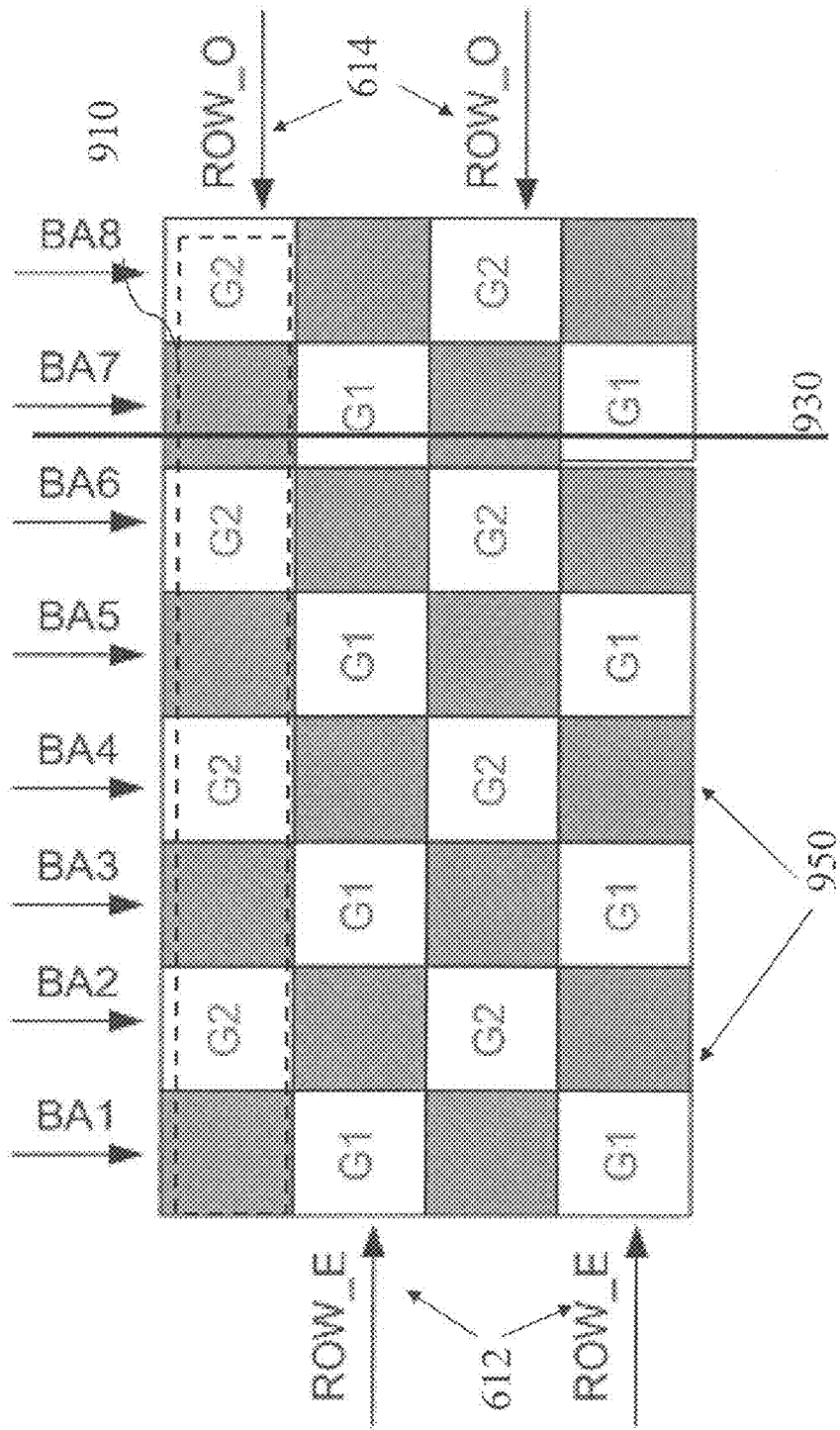
FIGS. 9A-9B are diagrams that show a portion of an exemplary DR imaging array including an embodiment of pixel unit cells according to the application.
Figure 9B:
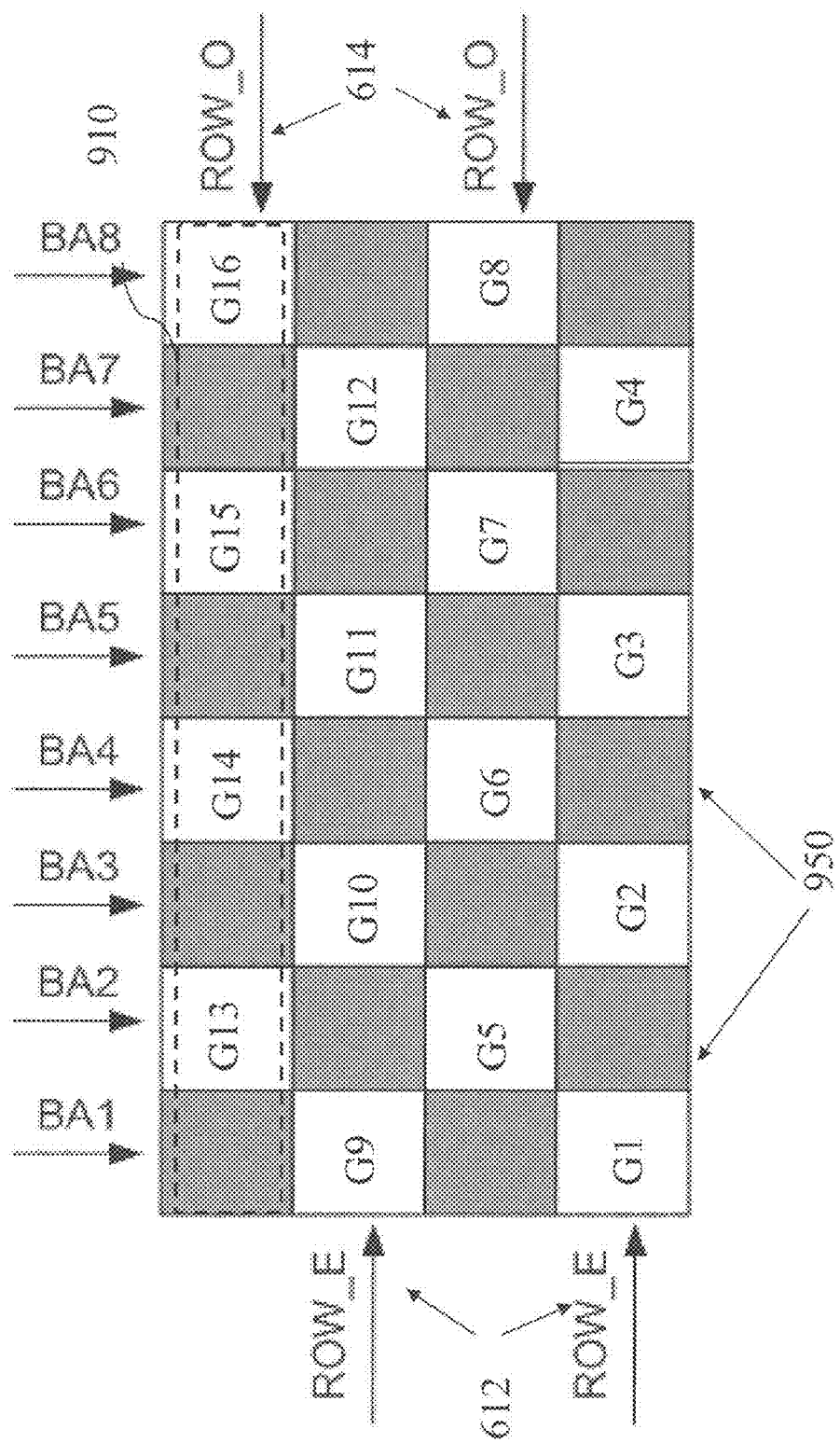

FIG. 9A is a diagram that shows a portion of an exemplary DR imaging array including an embodiment of pixel unit cells according to the application. Pixel unit cells 910 can be 8 pixels elements wide and can use 9 switching elements. As shown in FIG. 9A, relative to the exemplary by-2 subsampling approach over N sub-frames of FIG. 8, different exposure gain settings can be implemented for each of the sub-frames (e.g., with existing ROIC architectures and ROIC timing configurations). Exemplary grey regions 950 can represent unused or not-required pixel elements. As shown in FIG. 9A, a dual exposure gain configuration for a by-2 sub-sampling can be implemented. Two gain settings G1 and G2 can result in a 2 dimensional repeat pattern. A single dataline 930 can be used (e.g., vertical) for any pixel unit cell pattern up to a pattern of N photosensors. Further, in an embodiment shown in FIG. 9B, up to 2N exposure gain settings (e.g., independent and/or different) can be used. Gain can be changed along a row of an imaging array (e.g., between sub-frames) that can be changed between sub-frame readouts.

Figure 10:
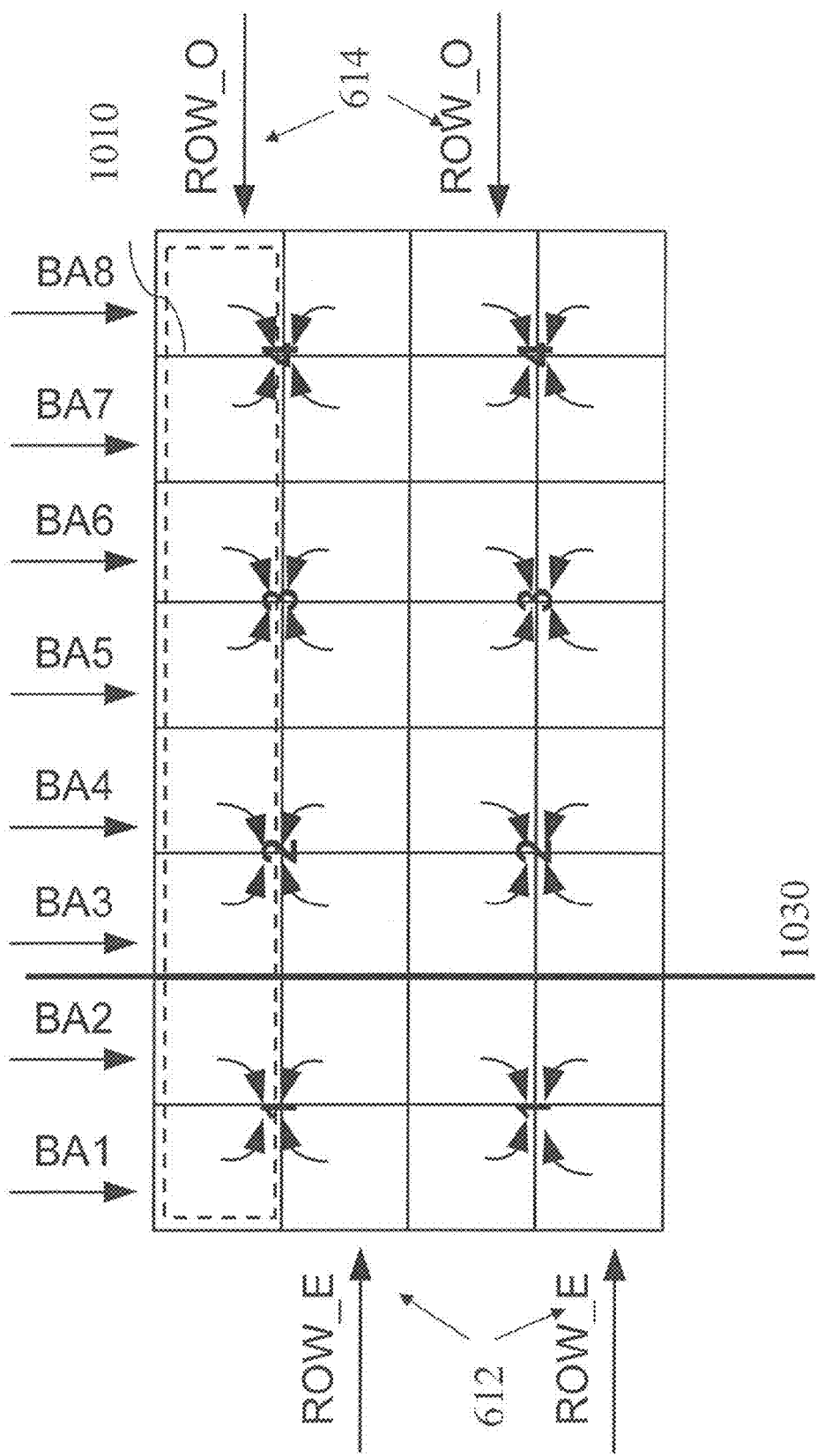
FIG. 10 is a diagram that shows a portion of an exemplary DR imaging array including an embodiment of pixel unit cells according to the application.

FIG. 10 is a diagram that shows a portion of an exemplary DR imaging array including an embodiment of pixel unit cells according to the application. Pixel unit cells 1010 can be 8 pixels elements wide and can use 9 TFTs. As shown in FIG. 10, a by-4 charge binning configuration can be implemented according to the application. Each 2×2 combination requires simultaneous clocking of the left and right shift register as well as a pair of block address control signals (e.g., BA<1>, BA<2>, . . . , BA<8>) simultaneously. In this configuration it takes N/2 sub-frames to readout all pixel elements. A single dataline 1030 can be used (e.g., vertical) for any pixel unit cell pattern up to a pattern of N photosensors.

Figure 11:
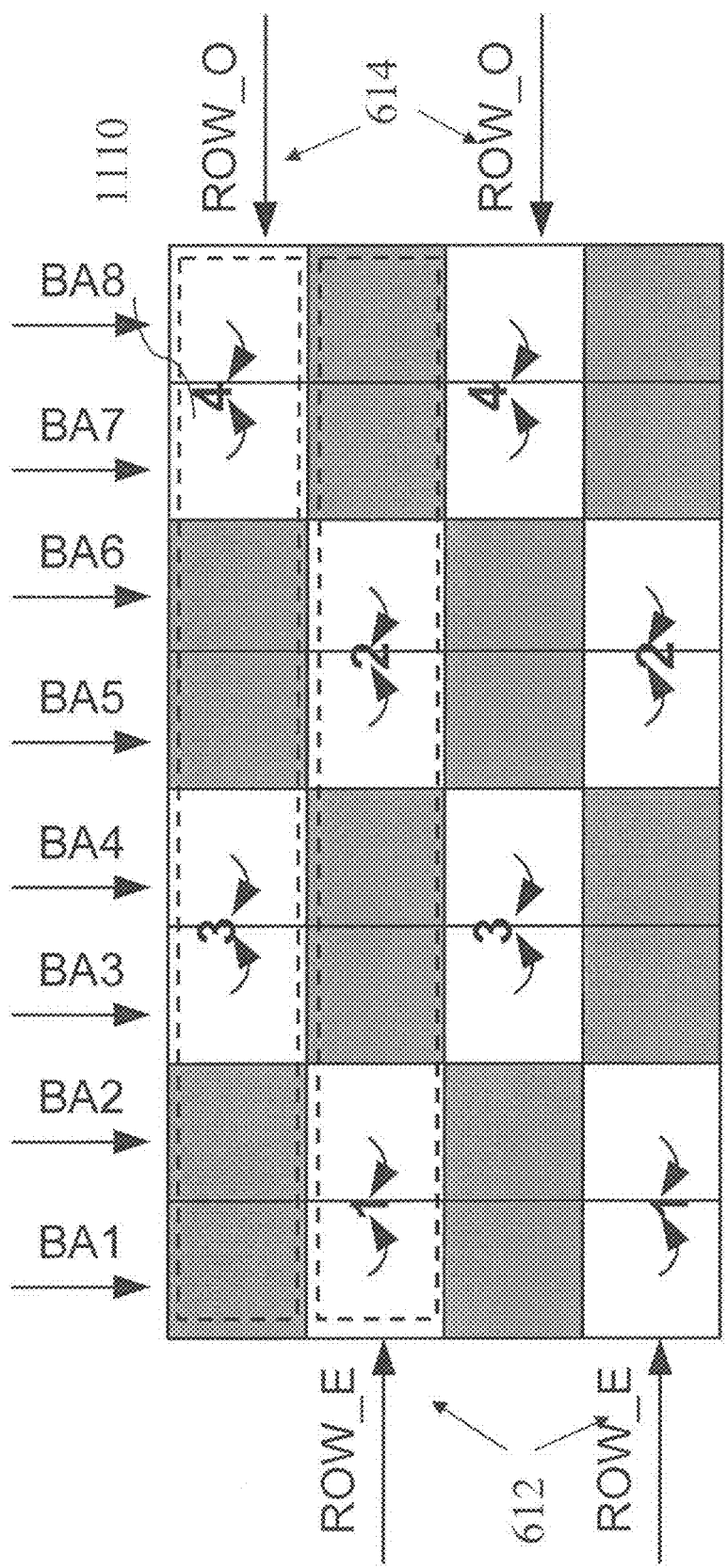
FIG. 11 is a diagram that shows a portion of an exemplary DR imaging array including an embodiment of pixel unit cells according to the application.

FIG. 11 is a diagram that shows a portion of an exemplary DR imaging array including an embodiment of pixel unit cells according to the application. Pixel unit cells 1110 can be 8 pixels elements wide and can use 9 switching elements. As shown in FIG. 11, a combination of by-2 charge summing and by-2 sub-sampling. The left shift register 612 can be used for 2 sub-frame readouts. A first subframe can use block address signals 1 and 2 together, and a second subframe can then use block address control signals 5 and 6 together. The next 2 subframes readouts can use the right shift register 614 where a first subframe can use block address signals 3 and 4 together, and a second subframe can then use block address control signals 7 and 8 together. In the exemplary configuration shown in FIG. 11, N/2 sub-frames can be used to readout all required pixel elements.

Embodiments according to the application can implement (e.g., first) subframe flushing. After light exposure, a first frame can be read having no block address pixels on, which can be used to reset any undesired charge as a function of light hitting switching elements. Embodiments using sub-frame flushing can also be used in subsampled modes where the un-used or not-required pixels can also be included in the first subframe flush. In embodiments using a two shift register approach, one first subframe flush can be used for the left shift register and one first frame flush can be used for the right shift register.

A disadvantage of the pixel design of FIG. 5A is an increase in charge transfer time from the photodiode to the dataline as compared to the prior art pixel design of FIG. 2. The time constant for charge transfer from the photodiode $\tau_{RC}$ is the product of the resistance of the TFT(s) $R_{TFT}$ and the photodiode capacitance $C_{PD}$. In the case where the block address TFT and the row select TFT are identical, the charge transfer time constant for the block address architecture of FIG. 5A is double the charge transfer time constant for the single TFT pixel of FIG. 2. This disadvantage may be overcome by a pixel design which includes a capacitor.

Figure 12A:
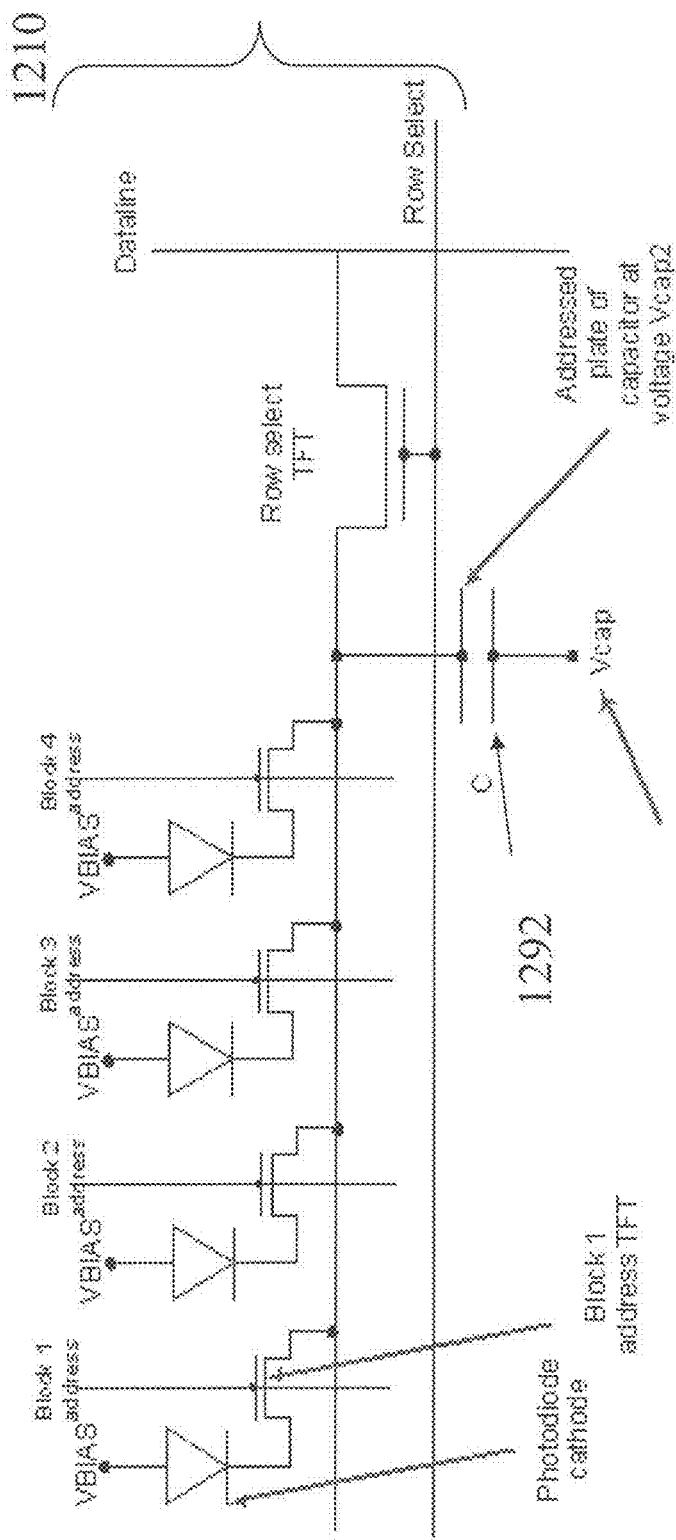
FIGS. 12A-12B are diagrams that shows a portion of an exemplary DR imaging array including an embodiment of pixel unit cells according to the application.
Figure 12B:
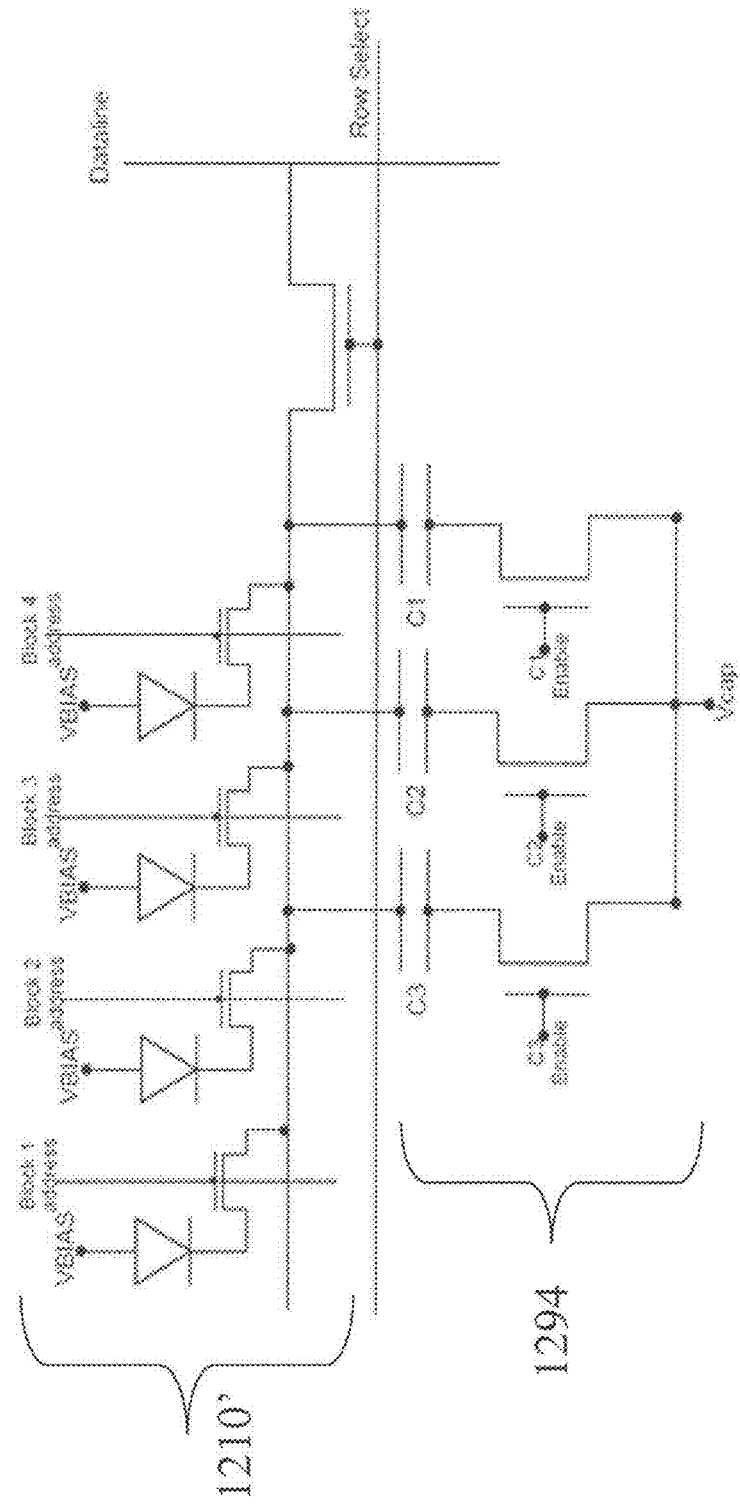

FIGS. 12A-12B are diagrams that shows a portion of an exemplary DR imaging array including an exemplary pixel unit cell embodiment. As shown in FIGS. 12A-12B, additional capacitance can be added to a pixel unit cell to increase the readout rate when the imaging array is operated in exemplary manners described herein. As shown in FIG. 12A, a capacitor 1292 with capacitance $C_{CAP}$ can be added to a pixel unit cell 1210. A common voltage $V_{CAP1}$ is applied the non-addressed plate of all capacitors in the imaging array. In order to reduce or minimize charge transfer time, thereby increasing readout rate, $C_{CAP}$ could be chosen to be less than the photodiode capacitance. Significantly reduced charge transfer times may be achieved by choosing $C_{CAP} \ll C_{PD}$, such as 25% or even 10% of $C_{PD}$. As shown in FIG. 12B, a switched capacitor bank 1294 can be added to a pixel unit cell 1210' where the capacitance (e.g., c1, c2, c3) can be selected based on characteristics such as the imaging modality or expected dosage.

Further, additional operating modes can operate using the pixel unit cell as shown in FIGS. 12A-12B. For example, a first operating mode can transfer the change from the first block of photosensors/photodiodes to the capacitors at the start of a block address (e.g., block 1 address). This operating mode comprises four steps: photodiode reset, exposure, block 1 charge transfer and block 1 readout; the block charge transfer and block readout steps being repeated sequentially for each of the other blocks:

(a) Photodiode reset: The photodiode cathode is reset to a voltage $V_{CATHODE}$ by setting the gates of all row select transistors into an "on" or conducting state, and the voltage on gates of all block address transistors $V_{BAG}$ to a voltage $V_{BAG} - V_T = V_{CATHODE}$ where $V_T$ is the threshold voltage of the block address transistors. In this mode, the detector is prepared for start of exposure at any time an X-ray exposure is requested by the radiographic technician.

(b) Charge integration and exposure: The imaging array is exposed to light. The addressed plate of the capacitors in each pixel are reset to a voltage $V_{CAP2}$ by turning the gates of all reset transistors into a conducting state and setting the dataline voltage to $V_{CAP2}$, where $V_{CAP2} > V_{CATHODE}$. In general, $V_{CAP2}$ can be chosen such that $V_{CAP2} > V_{CATHODE} + qN_{MAX}/C$, where $N_{MAX}$ is the maximum number of charge carriers anticipated during the exposure (c) Transfer of block 1 photo-charge to capacitors: The charge from the first block of photodiodes is transferred to the capacitors by setting the block address transistors of block 1 to $V_{BAG}$. Since $V_{CAP2} > V_{CATHODE} + qN_{MAX}/C$, all the photo-charge will be transferred from the diode to the capacitor, (d) Readout of block 1 photo-charge: The dataline is set to voltage $V_{CAP2}$. The row select transistors are serially addressed in order to transfer the charge from the capacitor to the photodiode. The time constant of the charge transfer from the capacitor to the photodiode is given by $\tau = R_{TFT} C_{CAP}$, which is a reduction by 2× for the case where $C_{CAP} = C_{PD}$, or 4× for $C_{CAP} = C_{PD}/2$, or 8× for $C_{CAP} = C_{PD}/4$. Of course, the capacitor value $C_{CAP}$ and the voltage $V_{CAP2}$ should be selected so as to ensure that the capacitor can hold the selected or maximum expected photo-charge from the chosen imaging modality: $C_{CAP} * (V_{CAP2} - V_{CATHODE}) > qN_{MAX}$.

The transfer step c and the readout step d is repeated for the remaining blocks, after which the imaging array is ready for the next exposure or for capture of dark reference frames for dark offset correction.

The photodiode reset period (a) in the operating mode described above may be used for sensing the start of radiographic exposure. Since all of the block address gates and row select gates are in a conducting state, any photocharge incident upon any of the diodes is transferred onto the respective datalines. Sensing a change in current in the readout circuits would be indicative of a start of exposure. Sensing a change in current would trigger the transition from the reset state (a) to the exposure state (b). This would allow radiographic exposures to occur without timing synchronization between the X-ray generator and the detector.

In an additional mode for sensing the start of exposure, the row select transistors may be maintained in an "off" state once the photodiodes and capacitors have been reset in period (a). The current on the common plate of the capacitor is sensed. At the start of exposure, the photo-charge begins to accumulate on the addressed plate of the capacitor; mirror charge flows from the power supply of the common plate onto the common plate of the capacitors. Sensing the start of current flow could be used to trigger the transition from the exposure sensing to step (b)—charge integration.

The imaging mode described above applies to static radiographic imaging applications, in which isolated single exposures are obtained. A second operating mode would apply to dynamic imaging applications, in which the radiographic exposure is continuous, such as fluoroscopy. In this operating mode the photodiode reset (a) and the exposure period (b) may be eliminated. The photodiodes are continuously exposed and the charge readout is also performed continuously, with the readout also serving to reset both photodiode and the capacitor.

It will be apparent to ones skilled in the art that alternative operating modes can be used with this architecture, For example, the common plate of the capacitor may be clocked either globally or on a block-sequential mode rather than held at a DC potential to facilitate charge storage and/or charge transfer.

In one embodiment, an imaging array for a DR detector can be configured with a single block rather than multiple blocks (e.g., the pixel architecture of FIG. 12A with a single block 1) where the block address gate is a transfer gate, which can be used for dynamic imaging applications.

Although embodiments of the application have been shown with a passive pixel architecture for the DR imaging array, various active pixel structures can be used for the individual pixels in the pixel block or pixel unit cell described herein. Further, although embodiments of the application have been shown with a pixel architecture that can include a single photosensor and a single TFT for the DR imaging array, various pixel structures using 2 TFTs, 3 TFTs, 4 TFTs, 5 TFTs, 6 TFTs, 7 TFTs or more TFTs with the single photosensor can be used for the pixel block or pixel unit cell described herein.

Embodiments of systems and/methods using pixel unit cells described herein contemplate methods and program products on any computer readable media for accomplishing its operations. Certain exemplary embodiments according can be implemented using an existing computer processor, or by a special purpose computer processor incorporated for this or another purpose or by a hardwired system.

Exemplary embodiments herein can be applied to digital radiographic imaging panels that use an array of pixels comprising an X-ray absorbing photoconductor, such as amorphous Selenium (a-Se), and a readout circuit. Since the X-rays are absorbed in the photoconductor, no separate scintillating screen is required.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Certain exemplary embodiments herein can be applied to digital radiographic imaging arrays where photoelectric conversion elements include at least one semiconductor layer, and that at least one semiconducting layer can include amorphous silicon, micro-crystalline silicon, poly-crystalline silicon, single-crystal silicon-on-glass (SiOG), organic semiconductor, and metal oxide semiconductors. Certain exemplary embodiments herein can be applied to digital radiographic imaging arrays where switching elements include at least one semiconductor layer, and that at least one semiconducting layer can include amorphous silicon, micro-crystalline silicon, poly-crystalline silicon, single-crystal silicon-on-glass (SiOG), organic semiconductor, and metal oxide semiconductors. Certain exemplary embodiments herein can be applied to digital radiographic imaging arrays where the DR detector is a flat panel detector, a curved detector or a detector including a flexible imaging substrate.

The array 212 can be divided into a plurality of individual cells 222 that can be arranged rectilinearly in columns and rows. As will be understood to those of ordinary skill in the art, the orientation of the columns and rows is arbitrary, however, for clarity of description it will be assumed that the rows extend horizontally and the columns extend vertically.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, \ solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A projection radiographic imaging array, comprising:
   an insulating substrate;
   a scan line to extend in a first direction over the insulating substrate;
   a data line to extend in a second direction over the insulating substrate; and
   a thin film pixel unit cell comprising
      a first thin film switching element comprising:
         a first terminal;
         a second terminal electrically coupled to the data line; and
         a control terminal electrically coupled to the scan line,
   where the first terminal and the second terminal are electrically coupled based on a scan signal from the scan line;
      a plurality of N pixel elements each comprising a photoelectric thin film conversion element and a second thin film switching element, where the photoelectric conversion element and the second switching element are connected in series between a first reference voltage and a first terminal of the first switching element.

2. The radiographic imaging array of claim 1, where the photoelectric conversion element is a photosensor, and the pixel unit cell comprises an N-photosensor pixel block and N+1 switching elements.

3. The radiographic imaging array of claim 1, comprising a plurality of N block address lines that respectively connect to a control terminal of one of the plurality of N second switching elements.

4. The radiographic imaging array of claim 1, where a selected second switching element and the first switching element are both enabled to connect one photoelectric conversion element to a corresponding data line.

5. The radiographic imaging array of claim 1, where a number of data lines connections in the radiographic imaging array is less than a number of photoelectric conversion elements in a row extending in the first direction, where the number of data lines in the imaging array is reduced by a ratio of 1/N.

6. The radiographic imaging array of claim 1, comprising a plurality of N block address lines each electrically coupled to select one of the N second switching elements, where multiple block address control signals simultaneously enabled transfer a charge of multiple photoelectric conversion elements in the pixel unit cell to one data line for output at one time.

7. The radiographic imaging array of claim 6, where charge binning of pixel elements positions along the first direction is configured to increase a signal to noise (SNR) value of data output by the radiographic imaging array.

8. The radiographic imaging array of claim 6, comprising a plurality of N block address lines each electrically coupled to select one of the N second switching elements, where at least one block address control signal is not selected when outputting charge from the plurality of photoelectric conversion elements to sub-sample charge among the plurality of photoelectric conversion elements in the pixel unit cell, where addressing less than all of the second switching elements or skipping second switching elements in the pixel unit cell provides horizontal sub-sampling of the radiographic imaging array.

9. The radiographic imaging array of claim 1, comprising a plurality of N block address lines each electrically coupled to select one of the N second switching elements, where multiple block address control signals simultaneously enabled transfer a charge of multiple photoelectric conversion elements in the pixel unit cell to one data line for output at one time, where the first frame is read having no block address control signals enabled to reset the photoelectric conversion elements in the pixel unit cell, where the first frame is configured to use a subset of the multiple block address control signals to reset a corresponding subset of the photoelectric conversion elements in the pixel unit cell.

10. The radiographic imaging array of claim 1, comprising a plurality of N block address lines each electrically coupled to select one of the N second switching elements, where vertical photoelectric conversion element charge binning is performed by accessing multiple second switching element rows, where for M scan lines, multiple scan line select signals can be accessed simultaneously with multiple block address lines for vertical charge binning of the imaging array.

11. The radiographic imaging array of claim 1, where non-adjacent photoelectric conversion elements have their corresponding charge binned using the first switching element, a single data line and multiple block address signals.

12. The radiographic imaging array of claim 1, first photoelectric conversion elements from a plurality of pixel unit cells have their corresponding charge binned using multiple scan lines and multiple block address signals.

13. The radiographic imaging array of claim 1, comprising:
   a first shift register coupled to a first subset of scan lines; and
   a second shift register coupled to a second different subset of scan lines.

14. The radiographic imaging array of claim 13, where the first shift register and the second shift register are implemented in thin-film transistors on the imaging array.

15. The radiographic imaging array of claim 1, where a number of pixel unit cells is greater than three, greater than four or greater than five in the first direction or the second direction.

16. The radiographic imaging array of claim 1, where the second thin film switching element comprises:

a first terminal;
a second terminal electrically coupled to the first terminal of the switching element, and
a control terminal electrically coupled to an independent block address line, where the first terminal and the second terminal of the second switching element are electrically coupled based on a signal at the independent block address line; and where the photoelectric conversion element, comprises,
a first terminal electrically coupled to the first reference voltage, and
a second terminal electrically coupled to the first terminal of the second switching element; and
further comprising a reference voltage line to connect to the first reference voltage to the first terminal of a plurality of photoelectric conversion elements.

17. The radiographic imaging array of claim 1, further comprising a digital radiographic imaging apparatus comprising a x-ray source, an x-ray detector and control parameters input device, where the x-ray detector is portable and wireless or tethered, where the x-ray detector comprises a flat panel radiographic detector, a DR detector, a curved DR detector, or a flexible substrate.

18. The radiographic imaging array of claim 1,
where the photoelectric conversion element includes at least one semiconductor layer, and that at least one semiconducting layer is selected from the group of amorphous silicon, micro crystalline silicon, poly-crystalline silicon, single-crystal silicon-on-glass (SiOG), organic semiconductor, and metal oxide semiconductors,
where the switching element includes at least one semiconductor layer, and that at least one semiconducting layer is selected from the group of amorphous silicon, micro crystalline silicon, poly-crystalline silicon, single-crystal silicon-on-glass (SiOG), organic semiconductor, and metal oxide semiconductors.

19. The radiographic imaging array of claim 1, further comprising:
at least one imaging array comprising:
a plurality of pixel unit cells arranged in rows and columns, where the scan line and the data line are common to more than one pixel unit cell,
driving circuits coupled to a plurality of rows of the imaging array,
readout circuits coupled to a plurality of columns of the imaging array; and
a conversion screen configured to convert first radiation of one or multiple wavelength range into second different radiation of one or multiple wavelength range proximate to the plurality of pixel unit cells.

20. A method of forming a digital radiographic detector including an indirect imaging pixel array, the method comprising:
providing a scintillator for an indirect imaging pixel array;
providing an insulating substrate for the indirect imaging pixel array;
providing scan lines extending in a first direction;
providing data lines extending in a second direction; and
providing pixel unit cells, each pixel unit cell comprising
a first thin-film transistor element;
a plurality of N pixel elements each comprising pairs of photoelectric thin-film conversion element and a second thin-film transistor where each pair of the photoelectric thin-film conversion element and the second thin-film transistor are connected in-series between a first reference voltage and the first switching element,
where the first thin-film transistor selectively connects said each pair of the photoelectric conversion element and the second thin-film transistor to a single dataline within the pixel unit cell.

* * * * *